(12) United States Patent
Goix et al.

(10) Patent No.: US 7,485,888 B2
(45) Date of Patent: Feb. 3, 2009

(54) SINGLE DETECTOR MULTICOLOR PARTICLE ANALYZER AND METHOD

(75) Inventors: Philippe Goix, Oakland, CA (US); Paul J. Lingane, Oakland, CA (US)

(73) Assignee: Guava Technologies, Inc., Hayward, CA (US)

( * ) Notice: Subject to any disclaimer, the term of this patent is extended or adjusted under 35 U.S.C. 154(b) by 28 days.

(21) Appl. No.: 10/821,727

(22) Filed: Apr. 8, 2004

(65) Prior Publication Data

US 2004/0252304 A1 Dec. 16, 2004

Related U.S. Application Data

(63) Continuation-in-part of application No. 10/461,538, filed on Jun. 12, 2003, now abandoned.

(51) Int. Cl.
*G01N 15/06* (2006.01)
*G01N 21/00* (2006.01)
*F21V 9/16* (2006.01)
*C02F 1/40* (2006.01)

(52) U.S. Cl. ............... 250/573; 250/458.1; 422/81; 204/602

(58) Field of Classification Search ............... 250/573, 250/574, 458.1, 459.1, 461.1, 461.2, 462.1; 356/318–320, 519, 454; 436/172; 422/81, 422/99; 204/602, 453
See application file for complete search history.

(56) References Cited

U.S. PATENT DOCUMENTS

| | | | | |
|---|---|---|---|---|
| 5,194,921 A | * | 3/1993 | Tambo et al. | ............... 356/432 |
| 5,567,294 A | * | 10/1996 | Dovichi et al. | ............... 204/603 |
| 6,091,843 A | | 7/2000 | Horesh et al. | |
| 6,210,973 B1 | * | 4/2001 | Pettit | ............... 436/172 |
| 2003/0017076 A1 | * | 1/2003 | Kochy et al. | ............... 422/81 |
| 2004/0096977 A1 | | 5/2004 | Rakestraw et al. | |

* cited by examiner

*Primary Examiner*—Georgia Y Epps
*Assistant Examiner*—Don Williams
(74) *Attorney, Agent, or Firm*—Houst Consulting

(57) ABSTRACT

A multicolor particle analyzer and method is described. The particles each of which either naturally fluoresce or are tagged to fluoresce at distinctive wavelengths are caused to flow through an analyzing volume where fluorescence is excited by an impinging light beam. A tunable optical filter repetitively and sequentially passes emitted light at each of the characteristic wavelengths as each particle travels through the analyzing volume and the light transmitted through the optical filter is received by single detector which provides output signals representative of each distinct wavelength of light emitted by the particle.

16 Claims, 5 Drawing Sheets

US 7,485,888 B2

SINGLE DETECTOR MULTICOLOR PARTICLE ANALYZER AND METHOD

RELATED APPLICATION

This application is a continuation-in-part of application Ser. No. 10/461,538 filed Jun. 12, 2003 now abandoned.

BRIEF DESCRIPTION OF THE INVENTION

The present invention relates generally to a multicolor particle analyzer or cytometer and method and more particularly to a multicolor particle analyzer and method which employs a single detector.

BACKGROUND OF INVENTION

Recent developments in flow cytometry hardware and dye chemistry has made it possible to simultaneously measure as many as ten or more fluorescences and scattered light parameters from cells, beads, molecules, etc. herein referred to as particles. They provide a large amount of novel information, which permits identification and characterization of cell subsets. However, such multicolor prior art systems are complex and expensive. They require multiple optical paths and detectors and complex control circuits. They are not suitable for portable use, point of care use or battlefield use.

Conventional flow cytometers require hydrodynamic sheath flow to align the particles in a single line in the laser probe volume. The hydrodynamic focusing accelerates the sample and particles and requires relatively large volumes of sample and sheath fluid to carry out an analysis. Typically for sample volume flow rates of 1 µL/s and exit velocities of 25-50 mm/s the particle velocities reach 10 m/s when they cross the probe volume. For a probe beam laser width of 20 microns, the particle time of flight through the probe volume is 2 microseconds. Since the particle is present in the probe volume for only a short time, a detection system of relatively large bandwidth is required for each color thus leading to complex, expensive and bulky systems.

OBJECT AND SUMMARY OF THE PRESENT INVENTION

It is an object of the present invention to provide a simple, relatively inexpensive multicolor particle detection system and method.

It is a further object of the present invention to provide a multicolor particle detection system and method, which employs a single detector.

It is a further object of the present invention to provide a multicolor particle detection system in which multiple reading of the distinct multicolor fluorescences of each particle is obtained during the time of flight of the particle through a probe volume in a capillary and therefore enables the reconstruction of the fluorescent traces of each particle using a single detector.

It is a further object of the present invention to provide a multicolor particle analyzer which employs an acousto-optical bandpass filter to repetitively sample fluorescent light at different wavelengths (color) in sequence as particles pass through the probe volume in a capillary.

The foregoing and other objects of the invention are achieved by a system in which the sample particles each of which fluoresce at one or multiple distinct wavelengths flow slowly through a capillary tube past a detection or probe volume where the particles are excited by a light beam and fluoresce at characteristic wavelengths. The fluorescent light is applied to an acousto-optical bandpass filter whose pass band repetitively changes wavelength multiple times as a particle passes through the probe volume and whose output is applied to a single detector. The output of the detector is reconstructed to provide a characteristic fluorescent trace for each fluorescent wavelength of the particle.

DESCRIPTION OF THE FIGURES

The foregoing and other objects of the invention will be more clearly understood from the following description when read in connection with the accompanying drawings of which.

DESCRIPTION OF PREFERRED EMBODIMENTS

Figure 1:
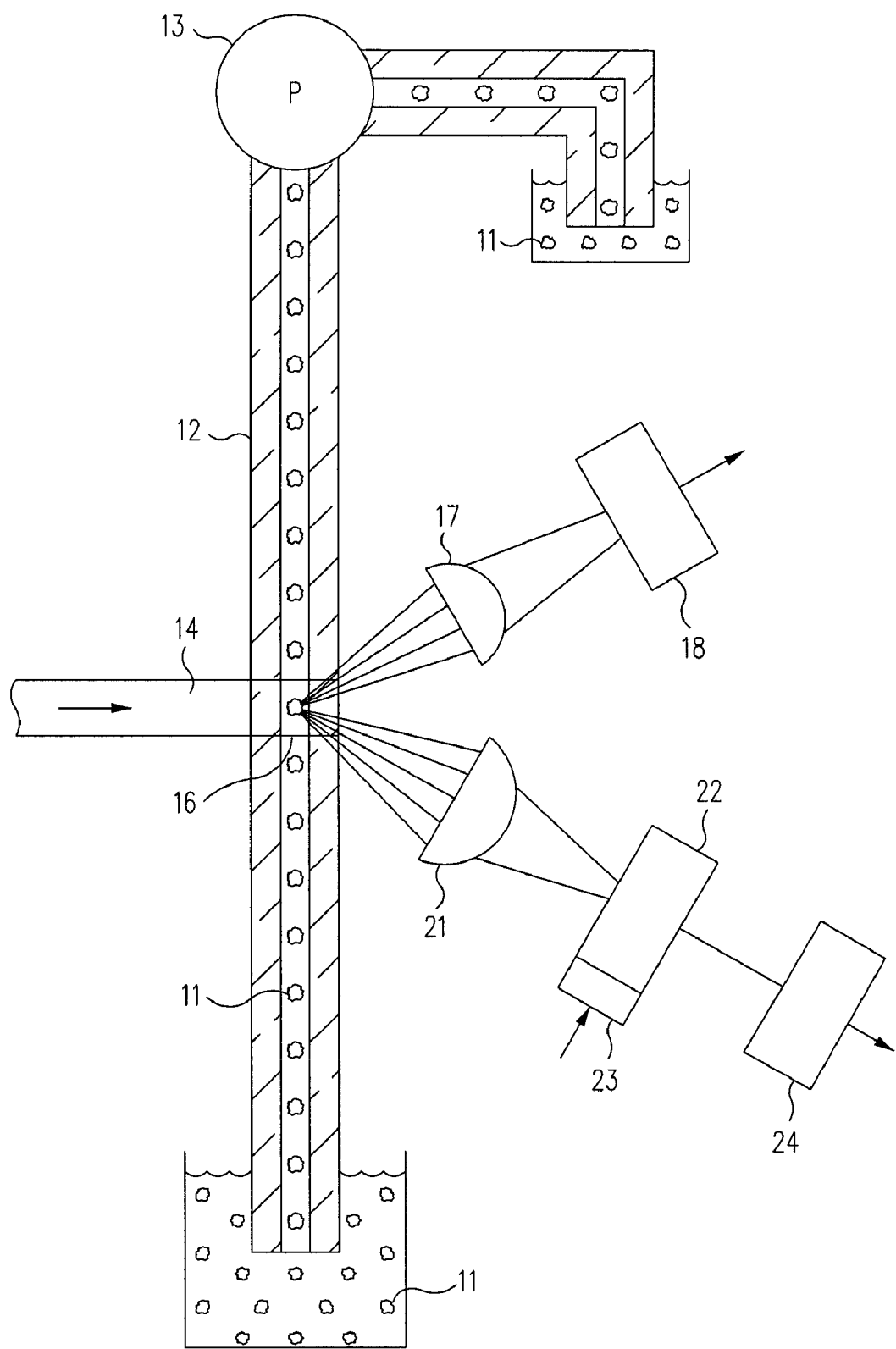
FIG. 1 is a schematic diagram of the multicolor particle analyzing system of the present invention.
Figure 5:
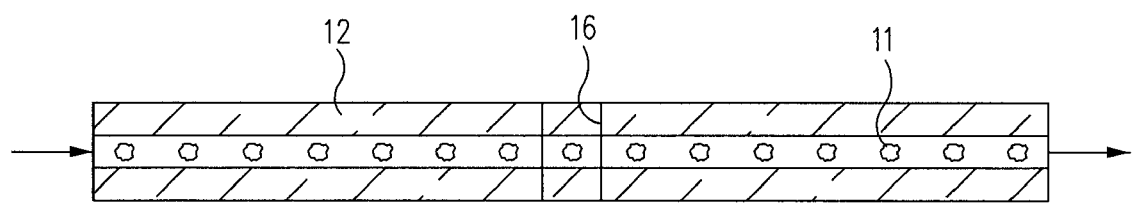
FIG. 5 shows flow through a capillary independent of whether the sample is aspirated or pumped.
Figure 3:
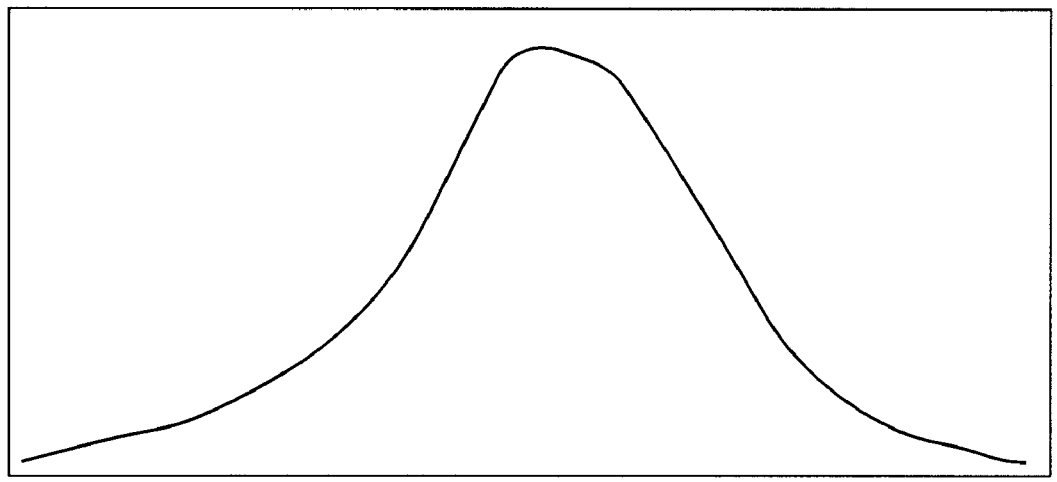
FIG. 3 is a scatter trace for a particle flowing through the analyzing volume.

A particle analyzing apparatus suitable for carrying out the invention is shown in FIG. 1. Briefly, a particle suspension 11 containing particles (as used herein "particles include cells, molecules, beads, etc.) to be analyzed flows through a capillary 12 as shown in FIGS. 1 and 5. Preferably the capillary is a square capillary. The sample with suspended particles is aspirated or drawn through the capillary by a pump 13. A laser or other suitable light source projects a beam 14 through the capillary to define an analyzing volume 16. The particle suspension flows through analyzing volume 16 with the cells singulated. Cells or particles, or beads which have been tagged with one or more dyes which fluoresce at distinct wavelengths are excited by the light beam 14 as they pass through the analyzing volume and emit light at the distinctive wavelengths. Scattered light is gathered by a lens system 17 and is focused onto detector 18 which provides a count of all particles which have traversed the volume whether labeled or not and information regarding their size. Cells which have been tagged or labeled with a distinct or characteristic dye or which naturally fluoresce emit light at the dye's corresponding wavelength. The light emitted by each tagged particles is gathered by a lens system 21 and applied to an acousto-optic tunable filter 22. The acousto-optic filter is driven by an integral transducer 23. The acoustic-optic filter is a solid-state electronically tunable band pass filter which uses acousto-optic interaction inside an anisotropic medium. It allows the user to select and pass or transmit a single tunable wavelength from the incoming light. The RF frequency applied to the transducer 23 controls the wavelength of the fluorescent light that is transmitted. The acousto-optic filter rapidly, sequentially and repetitively shifts the light wavelength which it passes so that as particles, cells or beads traverse the detection volume and emit fluorescent light at one or more characteristic wavelengths. The fluorescent light is periodically sampled and applied to the detector 24 a number of times for each wavelength during the transit time of that particle through the analyzing volume. Since the pass band is repetitively shifted and the process repeated during the transit time of a particle, the detector provides output pulses corresponding to the intensity of emitted fluorescent light at the characteristic wavelength of each label at the sampling intervals. As will be presently described, the signals can be reconstructed to provide a fluorescence trace for the particle. Since the wavelength pass band is repetitively shifted during passage of a particle the multiple wavelengths are sampled and detected whereby to provide multiple fluorescent traces for each particle.

Figure 2:
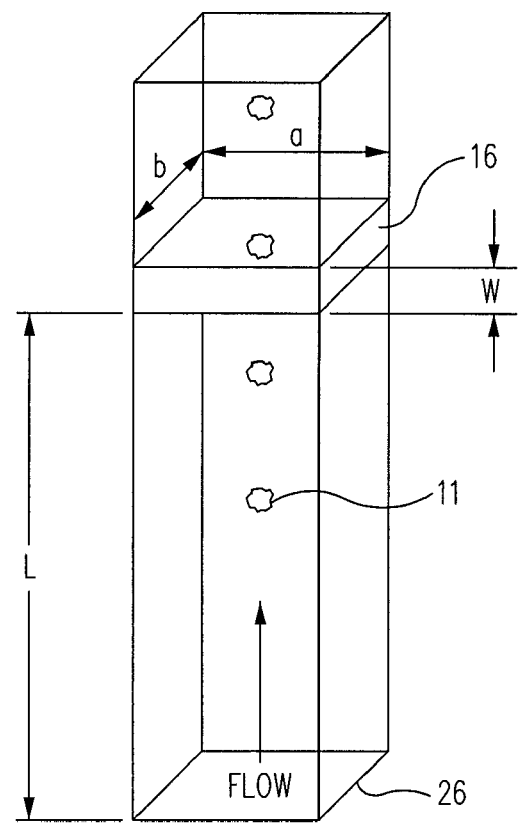
FIG. 2 is an enlarged view of a portion of the interior of the capillary shown in FIG. 1.

Referring particularly to FIG. 2, as a particle passes through the detection volume 16 the fluorescence is periodically detected when the wavelength pass band corresponds to the fluorescent wavelength of the particle. Assume the laser beam 14 has thickness of 20 µm and the capillary dimensions a=b=0.1 mm, and the volume of sample from the inlet 26 to the detection volume is 200 nanoliters and the probe volume is 0.2 nanoliters. Assume further that the flow rate is 1 microliter per second, then the particle velocity is 100 mm/s and the transit time through the detection volume is 200 µs. Assume that the acousto-optic filter can shift its pass band in 10 microseconds or less, this would result in sampling the fluorescent emission of each particle in a four color system about 5 times. It is apparent that if the acousto-optic filter can shift at a greater frequency, more samples can be taken or, in the alternative, a larger number of fluorescence colors can be detected and provide sufficient sampling points to reconstruct the fluorescence trace. It is also to be of particular note that the system requires small volumes of sample. The system is ideally suited for cell subset analysis wherein only small volumes of blood are available. This permits cell analysis which were, heretofore, difficult to perform because of the small volume of blood available, for example from infants, small animal species, mice, rats and other living organisms. The ability to analyze small volumes of blood from a living organism will allow characterization of blood cell populations without sacrificing the animals and will permit longitudinal studies where samples can be taken from a single animal at periodic intervals.

Figure 4:
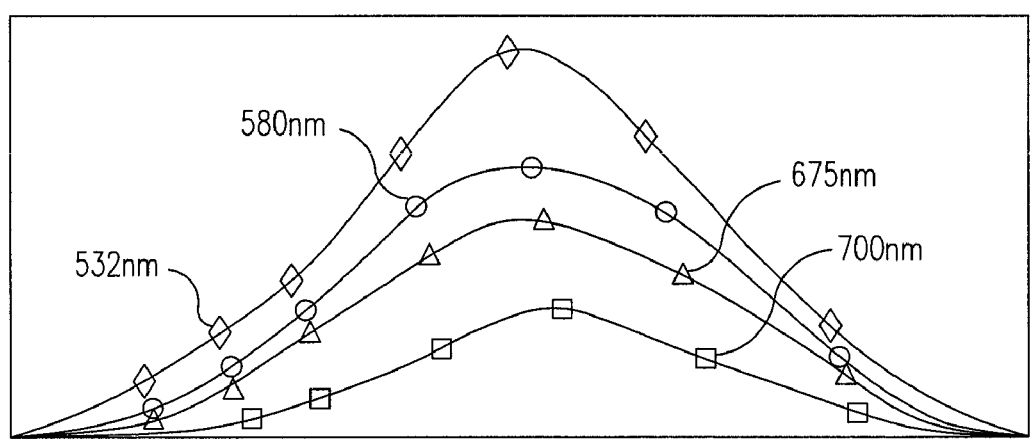
FIG. 4 shows the traces obtained from a particle tagged to fluoresce at four different wavelengths as it flows through the detection region.

For example, consider a sample with particles each of which have been tagged or naturally fluoresce at different wavelengths, say 532 nm, 580 nm, 675 nm and 700 nm, passing through the detection volume. The traces shown in FIG. 4 show the sampling points for each of four particles obtained by rapidly, sequentially, and repetitively detecting the fluorescence and using the sampling points to construct the traces for the four particles. It is seen that the amplitude of the signal increases as the particle travels into the detection volume and decreases as the particle leaves the detection volume. This provides a peak signal for each color.

Figure 6:
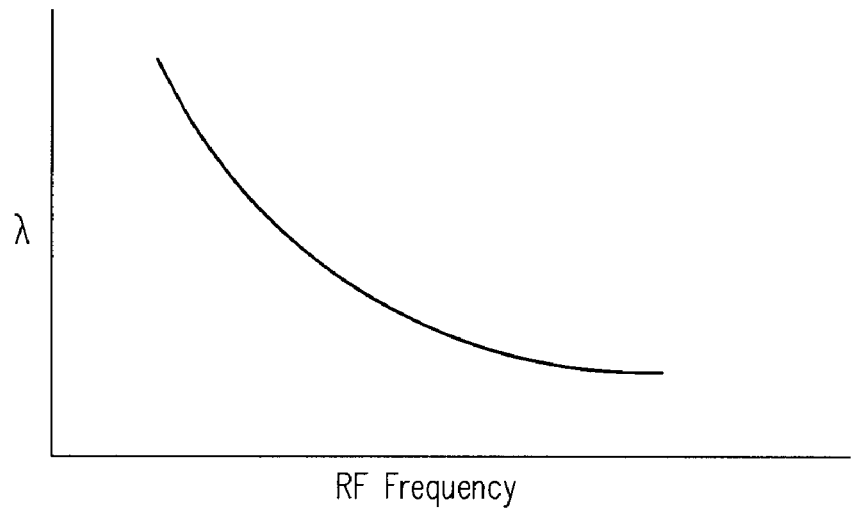
FIG. 6 shows the light wavelength pass bands of the acousto-optic filter as a function of the RF voltage frequency.
Figure 7:
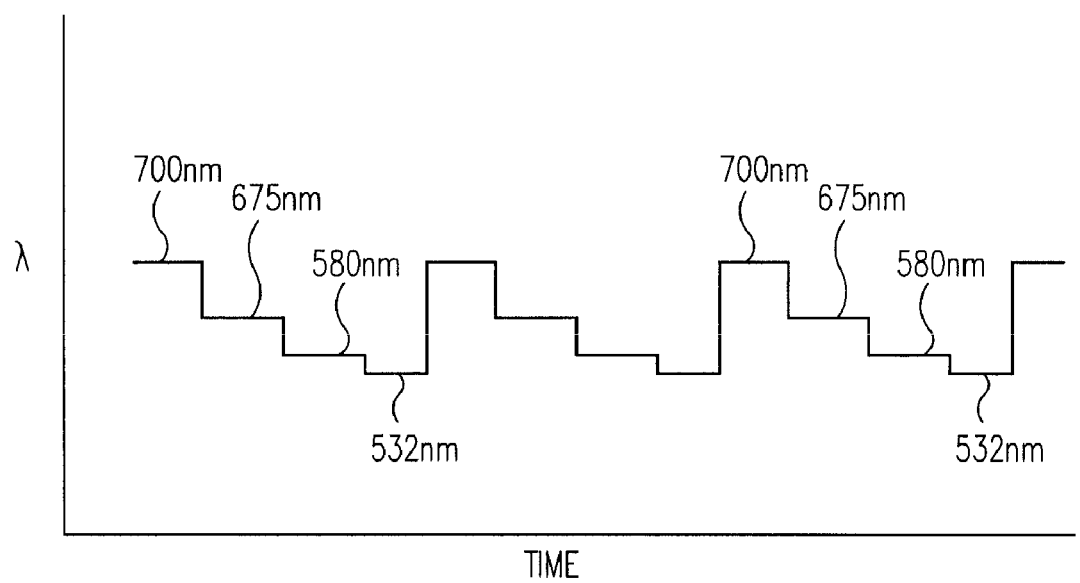
FIG. 7 show stepping the RF frequency to obtain sequential pass bands.
Figure 8:
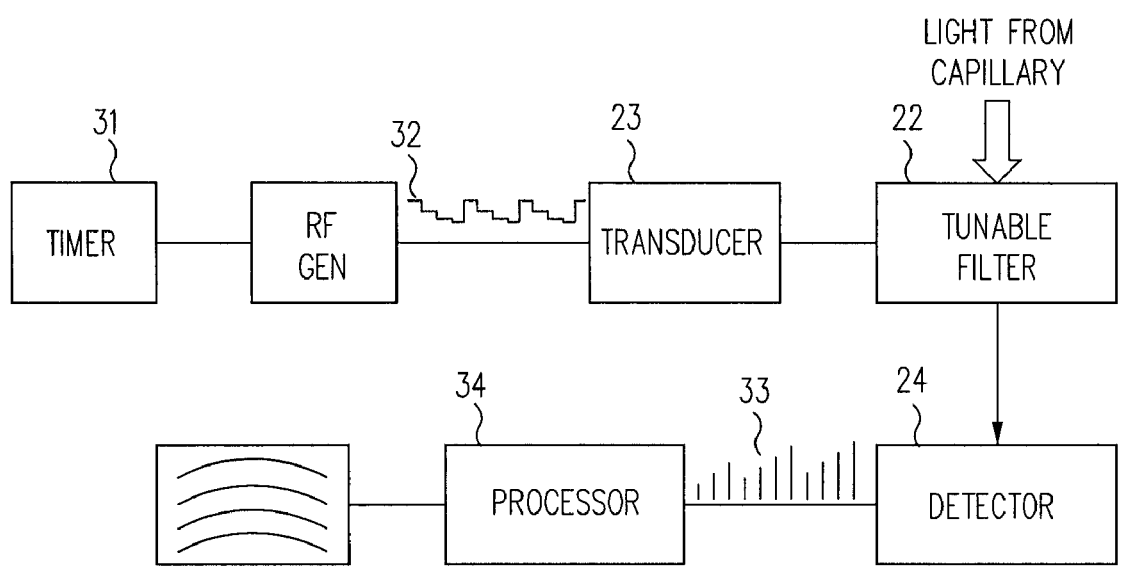
FIG. 8 is a schematic block diagram of a system for controlling the acquisition and detection of fluorescent light from a particle traveling through the analyzing region.

The acoustic-optic tunable filter passes light at a wavelength or frequency which is determined by the RF frequency of the drive voltage applied to the transducer 23. FIG. 6 is a schematic plot of pass wavelength as a function of the RF frequency applied to the transducer 23. If the RF frequency is periodically and repeatedly increased as shown in FIG. 7 the pass bands are also periodically and repetitively decreased in wavelength. As an example, the wavelengths of the pass bands for the above-noted wavelengths is illustrated in FIG. 7.

Should there be particles which emit at other wavelengths the RF frequency could be adjusted to drive the AO filter at the appropriate pass band wavelength. In other words, the AO filter could be tuned to the maximum spectral emission range of the particles. Although an AO filter is preferred other tunable filters could be used.

Referring to FIG. 7 a suitable circuit for controlling the tunable filter and constructing the traces for each particle is schematically shown. The circuit includes a source of timing pulses 31 which time the repetition of the RF frequency ramps 32. The transducer 23 is driven by the RF voltage ramps and drives the tunable filter 22 which receives the fluorescent light and selectively passes it to the detector 24. The detector provides output pulses 33 having an amplitude corresponding to that of the impinging light. A processor 34 synchronized by the timer receives the voltage pulses and reconstructs the traces, FIG. 4, for each wavelength. A peak detector (not shown) can provide a signal pulse representing the amplitude. The peak from a number of particles can then be plotted as a function of wavelength.

Thus there has been provided a particle analyzer using a single optical arrangement and detector to simultaneously measure a large number of fluorescent light parameters and provide information which permits characterization of particles which fluoresce at different wavelengths.

The invention claimed is:

1. A multicolor particle analyzer including:
 a capillary providing a predetermined detection volume;
 means for projecting a light beam through said capillary to illuminate said detection volume in said capillary;
 means for causing a fluid containing sample particles which naturally fluoresce or are tagged to fluoresce and emit light at one or more distinct wavelengths to flow along the capillary through said detection volume;
 a tunable filter adapted to sequentially shift pass band between two or more wavelengths multiple times as each particle passes through the illuminated detection volume, thereby when in operation the tunable filter sequentially passes emitted light at the two or more wavelengths in a predetermined direction; and
 a single fluorescence detector disposed in the predetermined direction for receiving and detecting the emitted light at the two or more wavelengths from said tunable filter and providing an output pulse for each particle passing through the illuminated detection volume.

2. A multicolor particle analyzer as in claim 1 in which the tunable filter is an acousto-optic filter.

3. A multicolor particle analyzer as in claims 1 or 2 including a detector for detecting light scattered by said particles as they travel through the predetermined detection volume.

4. The multicolor particle analyzer of claim 1 wherein the tunable filter is adapted to shift pass band between at least four wavelengths during the transit of each particle through the illuminated detection volume.

5. The multicolor particle analyzer of claim 1 wherein the tunable filter is adapted to shift pass band between wavelengths each at least five times during the transit of each particle through the illuminated detection volume.

6. The multicolor particle analyzer of claim 1 wherein the tunable filter is adapted to shift pass band between at least four wavelengths each at least five times during the transit of each particle through the illuminated detection volume.

7. A method of analyzing particles each of which fluoresces and emits light at multiple different distinct wavelengths responsive to excitation light which comprises the steps of:
 causing a fluid containing particles to be analyzed to flow through an analyzing region in a capillary;

applying excitation light to the analyzing region to cause each particle to emit light at its distinctive wavelengths as it passes through the analyzing region;

receiving the emitted light with a tunable optical filter said filter is adapted to sequentially shift pass band between two or more wavelengths multiple times as each particle passes through the analyzing region, thereby in a operation sequentially passing emitted light at the two or more wavelengths in a predetermined direction; and detecting the emitted light at the two or more wavelengths passed by the filter with a single fluorescence detector disposed in the predetermined direction to provide output signals representative of the distinct wavelengths.

8. The method of claim 7 wherein the particles are caused to flow at a rate such that the light emitted by a particle is passed by the tunable filter a number of times as the particle transits through the analyzing region.

9. The method of claim 7 wherein the tunable optical filter is adapted to shift pass band between at least four wavelengths during the transit of each particle through the analyzing region.

10. The method of claim 7 wherein the tunable optical filter is adapted to shift pass band between at least four wavelengths each at least five times during the transit of each particle through the analyzing region.

11. A particle analyzer for analyzing particles in a sample fluid which fluoresce and emit light at one or more wavelengths comprising:

a capillary for receiving a sample fluid containing particles to be analyzed and providing a predetermined analyzing region;

a pump for causing the sample fluid to flow through the capillary;

a light source for projecting a light beam through the capillary to illuminate said analyzing region along the capillary whereby singulated particles flow through the illuminated analyzing region and emit fluorescent light at the one or more wavelengths;

a tunable optical filter adapted to sequentially shift pass band between two or more wavelengths multiple times as each particle passes through the illuminated analyzing volume, whereby when in operation the tunable optical filter sequentially passes emitted light at the two or more wavelengths in a predetermined direction;

a single fluorescence detector disposed in the predetermined direction for receiving said light at the two or more wavelengths passing by the tunable filter and provide an output pulse for each particle passing through the illuminated analyzing volume; and a processor configured to receive said output pulse and provide an output signal representative of the amplitude of each of said one or more fluorescent wavelengths.

12. A particle analyzer as in claim 11 in which the tunable filter is an acoustic-optic filter.

13. The particle analyzer of claim 11 wherein the tunable optical filter is adapted to shift pass band between at least four wavelengths during the transit of each particle through the illuminated analyzing region.

14. The particle analyzer of claim 11 wherein the tunable optical filter is adapted to shift pass band between at least four wavelengths each at least five times during the transit of each particle through the illuminated analyzing region.

15. A method of analyzing particles in a fluid which fluoresce at one or more wavelengths comprising the steps of:

causing a fluid containing particles which fluoresce at one or more wavelengths to flow in a capillary past a source of illumination whereby the particles emit fluorescent light at the one or more wavelengths;

collecting the emitted light;

causing the collected emitted light to be incident on a tunable filter along a single predetermined direction;

sequentially shifting the passband of the tunable filter between two or more wavelengths multiple times as each particle passes through the illumination source;

repetitively detecting the emitted characteristic fluorescence of each of said particles multiple times during the transit of each of the particles through the illumination source using a single fluorescence detector disposed in the predetermined direction; and providing output signals representative of the characteristic wavelength of each of said particles.

16. The method of claim 15 wherein the emitted characteristic fluorescence of each of said particles is repetitively detected at least four times during the transit of each particle through the illuminated volume.

* * * * *

UNITED STATES PATENT AND TRADEMARK OFFICE
CERTIFICATE OF CORRECTION

PATENT NO.       : 7,485,888 B2
APPLICATION NO.  : 10/821727
DATED            : February 3, 2009
INVENTOR(S)      : Goix et al.

Page 1 of 1

It is certified that error appears in the above-identified patent and that said Letters Patent is hereby corrected as shown below:

Claim 7, column 5, line 7, please replace "in a operation" with -- in operation --.

Signed and Sealed this

Thirty-first Day of March, 2009

JOHN DOLL
*Acting Director of the United States Patent and Trademark Office*